United States Patent [19]
Fry

[11] 4,443,358
[45] Apr. 17, 1984

[54] NONCRYSTALLIZING AQUEOUS SOLUTIONS OF METAL SALTS OF NAPHTHALENE SULFONIC ACID-FORMALDEHYDE CONDENSATION PRODUCTS

[75] Inventor: Robert M. Fry, Raynham, Mass.

[73] Assignee: ICI Americas Inc., Wilmington, Del.

[21] Appl. No.: 441,780

[22] Filed: Nov. 15, 1982

[51] Int. Cl.$^3$ .......................... B01F 17/12; C04B 7/35
[52] U.S. Cl. ..................................... 252/353; 106/90
[58] Field of Search .................. 252/353, 354; 106/90, 106/99, 97

[56] References Cited

U.S. PATENT DOCUMENTS

| | | | |
|---|---|---|---|
| 3,686,133 | 8/1972 | Hattori et al. | 252/354 |
| 4,127,417 | 11/1978 | Okada et al. | 106/99 |
| 4,194,919 | 3/1980 | Hattori et al. | 106/90 |
| 4,238,236 | 12/1980 | Falcoz et al. | 106/90 |
| 4,257,814 | 3/1981 | Kellet et al. | 106/90 |

*Primary Examiner*—Richard D. Lovering
*Assistant Examiner*—Anne Brookes
*Attorney, Agent, or Firm*—Richard A. Rowe

[57] ABSTRACT

Aqueous solutions of naphthalene sulfonic acid/formaldehyde salts of at least two alkali metal ions remain substantially free of precipitate at temperatures of 0°–5° C.

12 Claims, No Drawings

NONCRYSTALLIZING AQUEOUS SOLUTIONS OF METAL SALTS OF NAPHTHALENE SULFONIC ACID-FORMALDEHYDE CONDENSATION PRODUCTS

The invention relates to noncrystallizing aqueous solutions of alkali/alkaline earth metal salts of naphthalene sulfonic acid/formaldehyde condensation products. Mixed alkali metal salts of high molecular weight condensation products of naphthalene sulfonic acid-formaldehyde containing about 40-60% by weight water are substantially stable against the formation of a crystalline precipitate at low temperatures of about 0°-5° C. These mixed salt solutions are particularly useful as dispersing agents when mixed with typical cement formulations to form a cement paste, mortar, concrete and the like.

Naphthalene sulfonic acid-formaldehyde condensation salts (hereinafter described as NSF) have been known for some time and have been fully described as cement dispersing agents in U.S. Pat. No. 3,686,133 and U.S. Pat. No. 4,194,919. Individual salts of sodium or potassium and the like have been used commercially as superplasticizers for concrete products. They are capable of effecting water reductions of 15-25% depending on the dosage used, the cement content and other factors. This means faster curing, reduced cement content and a shorter heated cure period for high strength concrete manufactures. Particular savings in energy costs for heat curing concrete at low temperatures are realized when the NSF surfactant is employed due to the shorter cure time and lower water content. Hydrated crystalline precipitates form at temperatures ranging from 0°-5° C. during storage of the NSF. The crystalline precipitate while not detrimental to the functionality of the surfactant in cement compositions does create problems when the aqueous solution is transferred from bulk storage containers because feed lines used to transfer the surfactant may clog with precipitate. While single salts solutions of potassium or sodium containing by-product sulfate and sulfonate salts form glassy crystalline precipitate at a temperature of 0°-5°, it has been suprisingly discovered that blends of the two salts at substantially the same concentrations do not form a precipitate thereby eliminating the problems associated with the cold storage of such materials.

It is the object of this invention to present an aqueous solution of a mixed alkali metal or ammonium salts of the condensation product of naphthalene sulfonic acid and formaldehyde which remains substantially free of precipitate at temperatures of 0°-5° C. over long periods. Another object of the invention is to present a method for the preparation of such salts.

Salts of high molecular weight condensation product NSF are remarkably effective in the dispersion of cement particles and are described in U.S. Pat. No. 3,686,133 where the dispersant contains only one metal ion M such as sodium, potassium or lithium as shown in general formula I. However, the salts of this invention are considered to be a blend of general formula I and general formula II as well as general formula III or a heterogeneous composition represented by formula III depending upon the preparative procedure used:

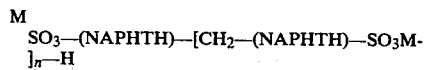

I

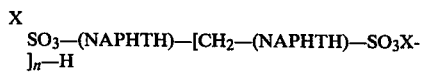

II

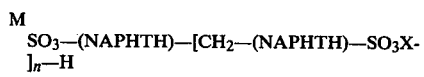

III wherein M is an ion interchangably selected from sodium, potassium, lithium, or ammonium and X is an ion different from M but interchangably selected from sodium, potassium, lithium, or ammonium ion provided that M and X are different in the blend, and NAPHTH is a naphthalene ring radical, and n has a value ranging from 5 to about 20 and preferably 9 to 12. It is understood that the naphthalene polymer chain is both linear and branched and mixtures thereof. The blends also contain minor amounts of similar by-product metal salts of sulfuric acid formed in the process of manufacture. The mol ratio of M/X in the surfactant solution may range from 1/3 to 3/1. The aqueous solution contains 30-60% by weight of the mixed salt including by-product salts. A composition containing 38-42% solids is usually preferred.

In general these materials are made by condensing molten naphthalene with fuming sulfuric acid to form naphthalene sulfonic acid derivatives having varying position isomers. The sulfonic acid derivative is then condensed with water and formaldehyde at temperatures of about 90° C. to form polynuclear condensation products having a general formula:

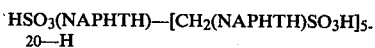

which are thereafter converted to a salt by the addition of at least two alkali metal, and/or ammonium hydroxides or carbonates either simultaneously or in sequence. Minor amounts of by-product sulfate salts are also formed. They can also be made by blending two or more salts each having a single cation ingredient. These materials are then diluted with water to form aqueous solutions having 30-60% solids (40-70% water). THe compositions may be further improved by the addition of alkaline earth or alkali metal salts of gluconic acid such as disclosed in U.S. Pat. No. 3,686,133, polyols and epoxy resins as described in U.S. Pat. No. 4,194,919 and processed into cement mixtures as described in U.S. Pat. No. 4,127,417.

Typical procedures for the preparation of the NSF surfactant solution are demonstrated but not limited to the following examples wherein all portions stated are parts or percent by weight or as otherwise specified.

Preparation A

In preparing the sodium salt 18,113 parts by weight of an NSF condensation melt having 49.7% by weight of a polynuclear product represented by the general formula:

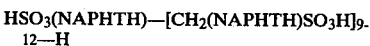

47.4% by weight water, 2.9% by water sulfuric acid and less than 1% unreacted formaldehyde was stirred for about 1 hour with 4598 parts of 50% sodium hydroxide which was added at a rate such that the temperature of the mix was maintained at about 71° C. After the addition of sodium hydroxide the pH of the solution was 3.7–4.0. The solution was further neutralized by the addition of 40 parts solid sodium carbonate to render the surfactant solution slightly alkaline. The aqueous solution contained 39.8% sodium sulfonate naphthalene/formaldehyde condensate salt, about 3.4% byproduct sodium sulfate and sulfonate salts and a total solids content of about 43.2%. Similar preparations using more or less water can be made having 30–60% by weight solids.

Preparation B

The potassium salt of the naphthalene sulfonic acid/formaldehyde condensate can be made according to the procedure of Preparation A wherein potassium hydroxide and carbonate is substituted in stoichiometoic proportions for sodium hydroxide and sodium carbonate using similar reaction conditions.

Preparation C

In order to make the ammonium salt of NSF surfactant a 28% ammonium hydroxide liquor may be substituted in appropriate stoichometric amounts for sodium hydroxide and carbonate in Preparation A and added at a temperature of 60°–80° C. until the pH in the range of 8.5–9.5 is reached.

EXAMPLE 1

A double salt of sodium and potassium was prepared by heating 300 grams of the NSF condensation melt described in Preparation A to 60° C. in a 500 milliliter glass round bottom flask, equipped with agitator, thermometer, pH meter, dropping funnel, condenser and heating mantle. Under mild agitating conditions 47.5 grams of potassium hydroxide liquor containing 21.39 grams (0.381 mol) was added to the melt over a period of one hour while maintaining the temperature in a range of 60°–80° C. The pH of the solution was approximately 1.0. A 50% sodium hydroxide liquor was then added under the same conditions until the pH reached the range of 3.5–5.5. To this 1.08 gram of sodium carbonate was added cautiously over 10–15 minutes at a temperature of 60°–80° C. and then further portions of sodium hydroxide liquor were added to bring the pH to 8.5–10.5. The total sodium hydroxide required was equivalent to 16.78 grams or 0.4195 mols. The mol ratio of sodium ion to potassium ion was approximately 1.1. Once the pH of the solution stabilized at a range of 8.5–10.5 total solids was estimated and diluted with water to 42%±2%. The resulting 366.2 grams of product had a total solid content of 42.1%, a pH 9.9, a viscosity of 29.18 centipoise and a concrete flow value of 151.5.

The concrete flow value is determined according to an ASTM Procedure C-305-65 Ref. to Sect. 2.1 where 500 grams of portland cement Type I containing 1.2% of the NSF dispersant is mixed with water, placed in a flow cone and permitted to flow out on a flat table and measured. The measured value is compared with a standard containing no dispersant

EXAMPLE 2

In order to make the sodium and ammonium mixed salts of NSF 1120 grams of condensation melt described in Preparation A was heated to 60° C. in a 2 liter round bottom flask equipped with agitator, thermometer, pH meter, dropping funnel, condenser and heating mantle. To this was added with mild agitation 122 grams of 50% sodium hydroxide (1.525 mol) at a temperature of 60°–80° C. over approximately 1½ hours. 206 Grams of 28% ammonium hydroxide liquor (1.648 mol) was then added at 60°–80° C. until the pH in the range of 8.5–9.5 was attained. The sodium ion/ammonium ion mol ratio of 0.93/1. The total solids content was adjusted with water to 40% to yield a total product weight of 1,434 grams having a pH of 9.1 and a concrete flow value of 185.7.

EXAMPLES 3 AND 4

According to the procedure of Example 1 using varying quantities of sodium hydroxide and potassium hydroxide, NSF compositions having a sodium ion/potassium ion ratio of 3/1 and 5.6/1 were prepared.

EXAMPLE 5–10

By blending various proportions of Preparation A with Preparation B and Preparation C by simple mixing procedures combinations containing sodium ion, potassium ion and ammonium ion blends having mol ratios ranging from 1/3–3/1 can be prepared.

Cold stability tests where run on the solutions of the preparations and the examples to measure stability. In one test solutions were stored for several weeks at 0° C. and compared visually for the amount of precipitate formed in the solution. The comparison is made against solutions containing only the sodium salts and only the potassium salts which have large amounts of precipitate and are rated the maximum of 10. In compositions showing no precipitation, a rating of 0 is given. Results for these tests are shown in Table 1.

Another freezing test was conducted wherein the samples were frozen solid at a temperature of −20° C. and thereafter removed from the freezer and permitted to thaw to room temperature after which they were rated for a precipitate. Results for the tests are shown in Table 1.

TABLE 1

NSF Low Temperature Stability Test

| Sample | Mol Ratio Na | / K / | NH$_4$ | Freeze Test 0° C. | Visual Ratings −20° C./20° C. |
|---|---|---|---|---|---|
| Prep A | 1 | 0 | 0 | 10 | 10 |
| Prep B | 0 | 1 | 0 | 10 | 10 |
| Prep C | 0 | 0 | 1 | 3–4 | 3–4 |
| Ex 1 | 1.1 | 1 | 0 | 0 | 0 |
| Ex 2 | 1 | 0 | 1.1 | 0 | 0 |
| Ex 3 | 3 | 1 | 0 | 2–3 | 3 |
| Ex 4 | 5.6 | 1 | 0 | 4–5 | 4–5 |
| Ex 5 | 2 | 1 | 1 | 1 | 1 |
| Ex 6 | 1 | 1 | 0 | 0 | 0 |
| Ex 7 | 0 | 1 | 1 | 0 | 0 |
| Ex 8 | 1 | 1 | 1 | 0 | 0 |
| Ex 9 | 3 | 1 | 0 | 2–3 | 2–3 |
| Ex 10 | 1 | 3 | 0 | 2–3 | 2–3 |

Typical cement formulations made from a dispersant of Example 1 were tested according to the procedures of ASTM-C-494 and meet the requirements for Type A water reducing and Type F high range water reducing chemical admixtures at dose rates of 13–19 fluid ounces per 100 pounds cement. The other exemplified materials are expected to exhibit similar results.

I claim:

1. An aqueous solution of a dispersing composition substantially free of precipitate at temperatures of 0°–5° C. which comprises 30–60% of a mixed salt blend of a high molecular weight condensation product of naphthalene sulfonic acid and formaldehyde having a general formula selected from at least two of the following:

MSO₃—(NAPHTH)—[CH₂(NAPHTH)—SO₃M-]ₙ—H     I

XSO₃—(NAPHTH)—[CH₂—(NAPHTH)—SO₃S]ₙ—H     II

MSO₃—(NAPHTH)—[CH₂—(NAPHTH)—SO₃X-]ₙ—H    III wherein M and X are different and interchangeably selected from at least two ions selected from the group consisting of Na, Li, K and NH₄; (NAPHTH) is a naphthalene radical; and n has a value of 5–20, and a minor amount of sulfate salts of said ions wherein the mol ratio of M/X ranges from 1/3 to 3/1.

2. A composition of claim 1 when made by reacting an aqueous solution of naphthalene sulfonic acid/formaldehyde condensation product having the general formula

HSO₃(NAPHTH)—[CH₂(NAPHTH)SO₃H]ₙ—H wherein n is 5–20 and (NAPHTH) is a naphthalene radical, containing unreacted sulfuric acid, with at least two hydroxides or carbonates selected from the group consisting of sodium, potassium, lithium and ammonium.

3. A composition of claim 2 when said hydroxides or carbonates are reacted in sequence.

4. A composition of claim 2 when said hydroxides or carbonate are reacted simultaneously.

5. An aqueous solution of a dispersing composition substantially free of precipitate at temperatures of 0°–5° C. which compises 30–60% of a mixed salt blend of a high molecular weight condensation product of naphthalene sulfonic acid and formaldehyde having a general formula selected from at least two of the following:

MSO₃—(NAPHTH)—[CH₂—(NAPHTH)—SO₃M-]ₙ—H     I

XSO₃—(NAPHTH)—[CH₂—(NAPHTH)—SO₃X-]ₙ—H    II

MSO₃—(NAPHTH)—[CH₂—(NAPHTH)—SO₃X-]ₙ—H    III wherein M and X are different and interchangeably selected from at least two ions selected from the group consisting of Na, K and NH₄; (NAPHTH) is a naphthalene radical; and n has a value of 5–20, and a minor amount of sulfate salts of said ions wherein the mol ratio of M/X ranges from 1/3 to 3/1.

6. A composition of claim 5 wherein M and X are the group consisting of Na+ and K+ ions.

7. A composition of claim 5 containing 38–42% of said salt blend, wherein M and X are the group consisting of Na and K and said ratio of M to X is about 1/1.

8. A composition of claim 5 wherein M and X are the group consisting of K and NH₄ ions.

9. A composition of claim 5 wherein M and X are the group consisting of Na and NH₄ ions.

10. A composition of claim 5 wherein M and X are the group consisting of Na, K and NH₄.

11. A composition of claim 5 when made by blending a composition of general formula (I) with a composition of general formula (II) wherein M is Na and X is K.

12. A composition of claim 5 when prepared by mixing a composition of claim 10 with a composition of general formula (I) wherein M is NH₄.

* * * * *

UNITED STATES PATENT AND TRADEMARK OFFICE
CERTIFICATE OF CORRECTION

PATENT NO. : U.S. 4,443,358
DATED : April 17, 1984
INVENTOR(S) : Robert M. Fry

It is certified that error appears in the above-identified patent and that said Letters Patent are hereby corrected as shown below:

Column 5, line 6 (structure II) reads

"$X SO_3-(NAPHTH)-[CH_2-(NAPHTH)-SO_3S]_n-H$"

should read

--$X SO_3-(NAPHTH)-[CH_2-(NAPHTH)-SO_3X]_n-H$--

Signed and Sealed this

Fourteenth Day of August 1984

[SEAL]

Attest:

GERALD J. MOSSINGHOFF

Attesting Officer

Commissioner of Patents and Trademarks